(12) United States Patent
Beardsley

(10) Patent No.: US 9,677,932 B2
(45) Date of Patent: Jun. 13, 2017

(54) FIELD LENS CORRECTED THREE MIRROR ANASTIGMAT SPECTROGRAPH

(71) Applicant: Burt J. Beardsley, Tucson, AZ (US)

(72) Inventor: Burt J. Beardsley, Tucson, AZ (US)

( * ) Notice: Subject to any disclaimer, the term of this patent is extended or adjusted under 35 U.S.C. 154(b) by 0 days.

(21) Appl. No.: 15/335,315

(22) Filed: Oct. 26, 2016

(65) Prior Publication Data

US 2017/0115163 A1    Apr. 27, 2017

Related U.S. Application Data

(60) Provisional application No. 62/246,398, filed on Oct. 26, 2015.

(51) Int. Cl.

| | |
|---|---|
| *G01J 3/28* | (2006.01) |
| *G01J 3/02* | (2006.01) |
| *G02B 17/08* | (2006.01) |
| *G02B 5/00* | (2006.01) |
| *G02B 27/30* | (2006.01) |
| *G02B 5/04* | (2006.01) |
| *G02B 5/18* | (2006.01) |
| *G01J 3/18* | (2006.01) |
| *G01N 21/25* | (2006.01) |
| *G01N 21/71* | (2006.01) |
| *G01J 3/12* | (2006.01) |

(52) U.S. Cl.
CPC ............ *G01J 3/021* (2013.01); *G01J 3/0218* (2013.01); *G01J 3/1809* (2013.01); *G01J 3/2823* (2013.01); *G01N 21/255* (2013.01); *G01N 21/718* (2013.01); *G02B 5/005* (2013.01); *G02B 5/04* (2013.01); *G02B 5/1842* (2013.01); *G02B 17/0848* (2013.01); *G02B 27/30* (2013.01); *G01J 2003/1208* (2013.01); *G01J 2003/284* (2013.01)

(58) Field of Classification Search
CPC ....... G01J 3/02; G01J 3/18; G01J 3/28; G02B 5/00; G02B 5/04; G02B 5/18; G02B 27/30; G01N 21/25; G01N 21/71
See application file for complete search history.

(56) References Cited

U.S. PATENT DOCUMENTS

2009/0091753 A1* 4/2009 Beardsley ............. G01J 3/0262
356/305

* cited by examiner

*Primary Examiner* — Abdullahi Nur
(74) *Attorney, Agent, or Firm* — Quarles & Brady LLP; Jiarong L. Lamiquiz

(57) ABSTRACT

A spectrograph that includes a first mirror having flat a mirror reflective surface and positioned to reflect light traversing a prism, a second mirror having a concave-shaped reflective mirror surface and positioned to reflect light received from the first mirror, a third mirror having a convex-shaped reflective mirror surface and positioned to receive light reflected by the second mirror, a fourth mirror having a spheroidal reflective mirror surface and positioned to receive light reflected by the third mirror, and a field lens comprising a concave mirror surface in combination with a convex mirror surface, wherein light received by said field lens from said fourth mirror enters said convex mirror surface, traverses said field lens, and exits from said concave mirror surface. The fifth mirror is positioned such that the second mirror, third mirror, fourth mirror, and fifth mirror share a common vertex axis.

16 Claims, 2 Drawing Sheets

FIELD LENS CORRECTED THREE MIRROR ANASTIGMAT SPECTROGRAPH

CROSS-REFERENCE TO RELATED APPLICATIONS

This non-Provisional Application claims priority from a United States Provisional Application filed 26 Oct. 2015 and having Ser. No. 62/246,398, which is hereby incorporated by reference herein.

FIELD OF THE INVENTION

This invention relates to optical instruments for use in the measurement of properties of light, and specifically to echelle spectrographs.

BACKGROUND OF THE INVENTION

An echelle spectrograph is a spectrograph which uses an echelle grating to diffract light at high resolutions and high diffraction orders. As with other blazed diffraction gratings, the echelle grating consists of a number of grooves, the width of the grooves being close to the wavelength of the diffracted radiation. However, echelle gratings are specifically characterized by the large spacing between the grooves and, therefore, comprises a lower groove density.

Light incident upon any blazed grating is split into several different diffraction orders. Each order will be comprised of a different but overlapping wavelength range. The dispersion associated with each order will also be different. The overlapping orders make it difficult to associate the correct order numbers with their wavelength ranges. This ambiguity complicates the spectrum and makes it more difficult to determine the correct wavelength emission from the source.

Although this overlap is generally an unwanted side effect, echelle gratings specifically use this effect to enhance the performance of the spectrograph. A second cross-dispersing element is used to spatially separate the orders. The individual orders, each with a separate (and sometimes overlapping) wavelength range and resolution, can then be analyzed without ambiguity.

Typical echelle spectrographs have a relatively high effective fvalue, generally f/7 or greater, limiting the total light which reaches the image plane and thereby decreasing the resulting image quality. Further, the high effective fvalue of typical echelle spectrographs prevent their use in certain applications such as Raman spectroscopy where the detection of weak emissions requires the use of a spectrograph with a very low fvalue. Clearly, it is desirable to design an echelle spectrograph with a low fvalue.

SUMMARY OF THE INVENTION

In one implementation, a spectrograph is presented. The spectrograph includes a first mirror having flat a mirror reflective surface and positioned to reflect light traversing a prism; a second mirror having a concave-shaped reflective mirror surface and positioned to reflect light received from the first mirror; a third mirror having a convex-shaped reflective mirror surface and positioned to receive light reflected by the second mirror; a fourth mirror having a spheroidal reflective mirror surface and positioned to receive light reflected by the third mirror; and a field lens comprising a concave mirror surface in combination with a convex mirror surface, wherein light received by said field lens from said fourth mirror enters said convex mirror surface, traverses said field lens, and exits from said concave mirror surface. The fifth mirror is positioned such that the second mirror, third mirror, fourth mirror, and fifth mirror share a common vertex axis.

BRIEF DESCRIPTION OF THE DRAWINGS

The disclosure will be better understood from a reading of the following detailed description taken in conjunction with the drawings in which like reference designators are used to designate like elements, and in which.

DETAILED DESCRIPTION OF THE PREFERRED EMBODIMENTS

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
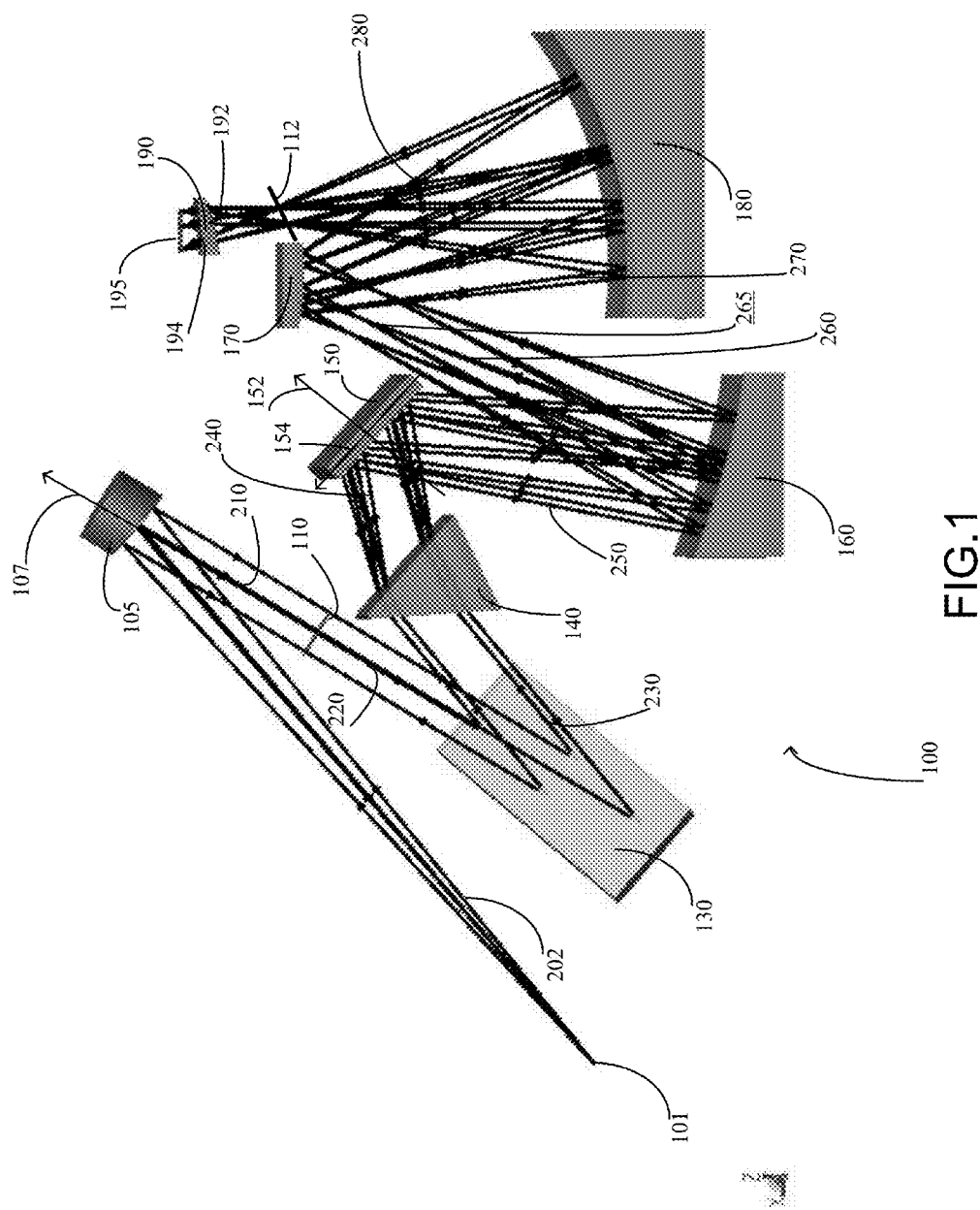
FIG. 1 illustrates the movement of radiation through Applicant's echelle spectrograph.
Figure 2:
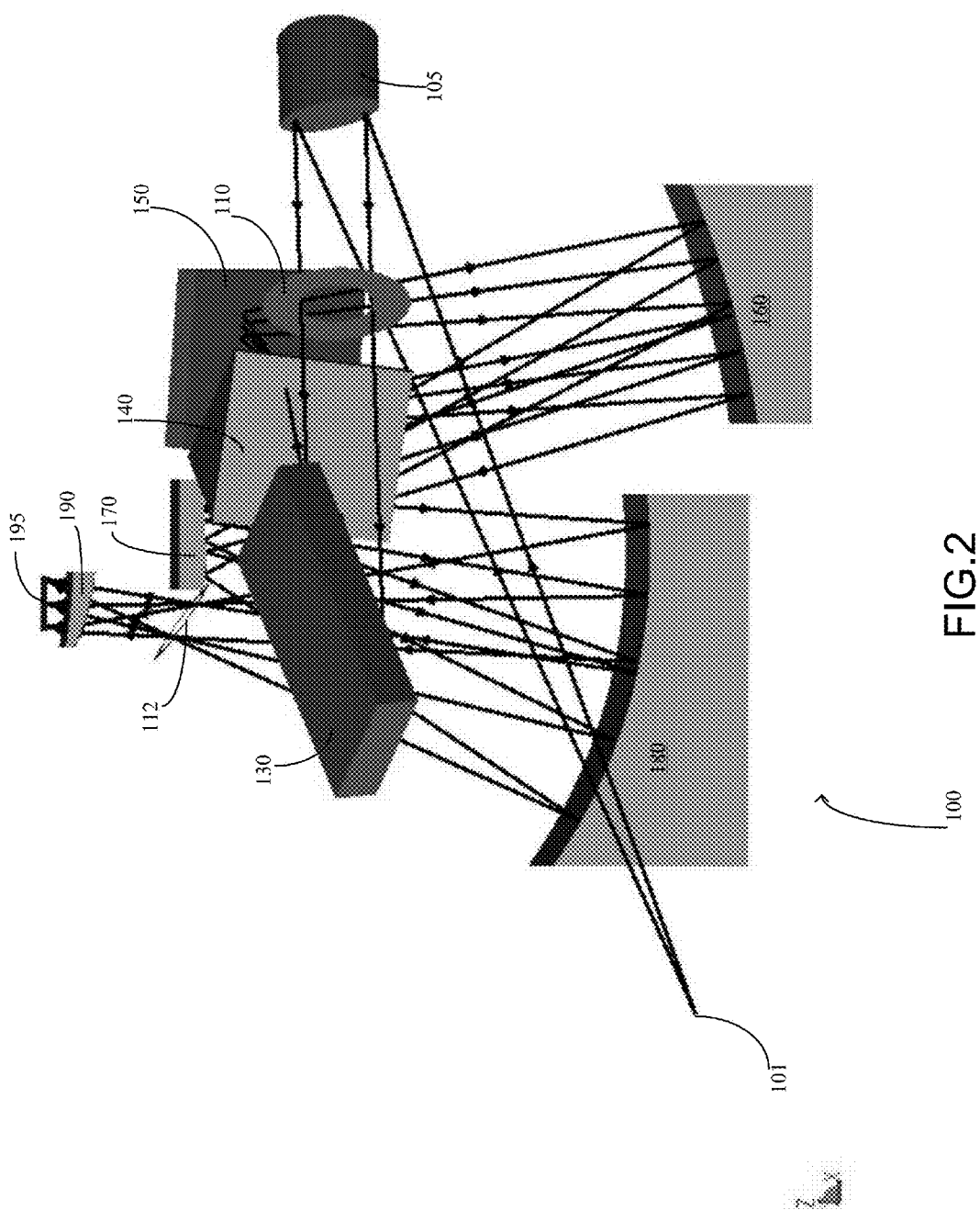
FIG. 2 shows a different perspective of the Applicant's echelle spectrograph.

Referring now to the illustrated embodiment of FIG. 1, Applicant's echelle spectrograph 100 comprises an entrance aperture 101, a collimating mirror 105 with its parent optical axis 107, a first aperture stop 110, a second aperture stop 112, a diffraction grating 130, a prism 140, a first mirror 150 having a flat mirror reflective surface with its first axis 152 and a second axis 154, a second mirror 160 having concave-shaped mirror surfaces, a third mirror 170 having convex-shaped mirror surfaces, a fourth mirror 180 having concave-shaped mirror surface, a field lens 190, and an image plane 195.

In certain embodiments, a cone of light enters through entrance aperture 101 and travels toward collimating mirror 105 as a cone of light 202. In the illustrated embodiment of FIG. 1, the collimating mirror 105 comprises a Conic Constant of −1 and Radius of Curvature of 72 mm (concave).

Light 202 is reflected off collimating mirror 105 to give collimated light 210. Collimated light 210 passes through aperture stop 110, which located on the parent axis 107 of the collimating mirror 105. In certain embodiments, collimating mirror 105 is interchangeable. This being the case, the focal length of collimating mirror 105 is adjustable. If entrance aperture 101 is located correctly, there are practically no aberrations in light 210, and therefore, light 210 comprises nearly perfect collimated light.

Light 210 passes through aperture stop 110 and produces light 220. Light 220 is directed onto diffraction grating 130. Light 220 comprises a polychromatic beam, i.e., light 220 comprises electromagnetic radiation containing a plurality of wavelengths. The nature of the light source determines the constituent wavelengths of light 220.

As those skilled in the art will appreciate, echelle grating 130 separates incident light 220 into a plurality of constituent wavelengths, i.e., light 220 is dispersed by echelle grating 130. When light 220 is incident on echelle grating 130 with an angle θi (measured from the normal of the grating), that light is diffracted into several beams. The beam that corresponds to direct transmission (or specular reflection in the case of a reflection grating) is called the zero order, and is denoted m=0. The other orders correspond to diffraction angles which are represented by non-zero integer values for m. For a groove period d and an incident wavelength λ, the grating equation (4) gives the value of the diffracted angle θm(λ) in the order m:

$$d(\sin \theta m(\lambda) + \sin \theta i) = M\lambda \quad (4)$$

The diffracted beams corresponding to consecutive orders may overlap, depending on the spectral content of the incident beam and the grating density. The higher the spectral order, the greater the overlap of light into the next order.

Light 230 that is reflected from diffraction grating 130 comprises a plurality of beams dispersed by wavelength. Light 230 is directed onto dispersive prism 140. As those skilled in the art will appreciate, light changes speed as it moves from one medium to another, for example, from air into the matrix of prism 140. Under Huygens principle, such a speed-change causes light striking the boundary between two media at an angle to be refracted and enter the new medium at a different angle.

In accordance with Snell's law, the degree of bending of a light path is a function of, inter alia, the ratio between the refractive indices of the two media. The refractive index of a medium varies with the wavelength of the light. This being the case, light 230 traveling through prism 140 is further dispersed by wavelength, but in a direction orthogonal to the dispersion direction of the grating.

Echelle grating 130 can be replaced with another grating of different groove density or blaze angle. Changing the blaze angle or groove density of grating 130 will provide different spectral characteristics at image plane 195 that will affect spectral resolution and order spacing. Echelle grating 130 is interchangeable with a wide range of groove densities and blaze angles that can be used in different embodiments.

Prism 140 controls the total range of wavelengths passing through to image plane 195. By changing prism 140, different wavelength ranges can be utilized at image plane 195. For example, the standard embodiment of echelle spectrograph 100 includes a fused silica (FS) prism 140. The wavelength range using the FS prism 140 is about 180 nm up to about 1.1 microns. If prism 140 comprises a CaF2 prism, the wavelength range can be extended down to about 150 nm. Another embodiment can include a BK7 glass prism 140. BK7 has higher dispersion than FS or CaF2 but it does not transmit light below 350 nm. The wavelength range of the echelle spectrograph 100 would be from about 350 nm up to about 1.1 microns, but the spectral order separation is larger because dispersion is higher with BK7 glass. A taller entrance aperture 101 can then be used to increase the etendue of the instrument for this embodiment with a BK7 glass prism 140.

Light 240 exits prism 140, and is directed onto the first mirror 150. The first mirror 150 comprises a flat mirror reflective surface. In certain embodiments, the first mirror 150 tilts along the first axis 152 thereof, then tilts along the second axis 154 thereof. The first mirror 150 is titled in a way such that no obstruction of light 250, 260, 270, and 280. Further, the first mirror 150 is disposed at an angle such that minimal obstructions occur with the grating 130 when mounting a camera. The image plane 195 is located within a sensor. In certain embodiments, a sensor is a scientific, digital CCD camera used to collect image data of the light from an emitting source. With this configuration of the first mirror 150, the dimension of the echelle spectrograph 100 is allowed to decrease and generate a hand-held echelle spectrograph.

Further, light 240 is reflected from the first mirror 150 as light 250. For any given wavelength, the beam is still collimated. However, each wavelength reflects off the first mirror 150 at a slightly different angle because of the dispersion by grating 130 and prism 140.

Light 250 is incident on the second mirror 160. In certain embodiments, the second mirror 160 comprises a radius of curvature of about 97.701 mm (concave) and a conic constant of −0.5631. In these embodiments, the second mirror 160 comprises an ellipsoidal mirror.

Light 250 is reflected convergingly and then divergingly from the second mirror 160 as light 260. Light 260 converges from the second mirror 160 to an intermediate focus 265 and then diverges from intermediate focus 265 until it strikes the third mirror 170. In certain embodiments, the intermediate focus 265 comprises a baffle, which is formed to include an aperture. The baffle is disposed in echelle spectrograph 100 such that light 260 converge from the second mirror 160, passes through said aperture in the baffle, and strikes the third mirror 170.

In certain embodiments, the third mirror 170 comprises a radius of curvature of about 70.086 mm (convex) and a conic constant of 0. In these embodiments, the third mirror 170 comprises a spheroidal convex mirror. In other embodiments, the third mirror 170 comprises an ellipsoidal (0.0>conic constant>−1.0, parabolic (conic constant=−1.0) or a hyperbolic (conic constant<−1.0) convex mirror.

Light 260 is reflected divergingly from the third mirror 170 as light 270, wherein light 270 passes onto the fourth mirror 180. In certain embodiments, the fourth mirror comprises an ellipsoidal (0.0>conic constant>−1.0), spherical (conic constant=0), spheroidal, or oblate spheroidal concave mirror (conic constant>0). In general, the smaller the conic constant (more negative), the better the correction but the larger the mirror and spectrograph becomes.

In certain embodiments, Applicant's echelle spectrograph utilizes a spherical mirror for the fourth mirror 180 rather than other conic surfaces. The resulting ease of fabrication of the spherical mirror has many important ramifications for Applicant's echelle spectrograph.

In certain embodiments, the fourth mirror 180 comprises a radius of curvature of about 78.916 mm (concave) and a conic constant of 0. In these embodiments, the fourth mirror 180 comprises a spheroidal mirror.

Light 270 is reflected convergingly from the fourth mirror 180 as light 280. Light 280 is directed onto a correcting, field lens 190 through a second aperture 112. In certain embodiments, the filed lens 190 is a meniscus lens. Light 280 first passes through first surface 192. In certain embodiments, surface 192 is spherical and convex. The light exits correcting lens 190 through second surface 194 to define image plane 195. In certain embodiments, second surface 194 is spherical and concave. Further, in certain embodiments, a field lens 190 parent vertex axis is located on the parent axis shared by the second, third, and fourth mirrors.

As those skilled in the art will appreciate, an aperture stop limits the brightness of an image by restricting the size of the angular cone of light passing through the entrance aperture. Therefore, aperture stops 110 is one of the primary parameters controlling the amount of light entering echelle spectrograph 100.

In certain embodiments, each of the aperture stops comprises an interchangeable device, such that the aperture stop 110 can be adjusted to allow a desired amount of light into echelle spectrograph 100. A smaller aperture stop will result in a sharper image at image plane 195 by reducing optical aberrations. Echelle spectrograph 100 can be optimized for maximum light throughput (large aperture stop 110) or maximum spectral resolution (small aperture stop 110).

One way to change the effective focal length (the "f" value of the input optics) of the echelle spectrograph 100 is to change the focal length of the collimating mirror 105. For purposes of this discussion, fvalue=1/(2× (sin θ)) where θ is the half angle of light passing through entrance aperture 101. The numerical aperture (NA) for entrance aperture 101 is defined as NA=sin (θ), or equivalently, $$NA=\sin [\arctan \{D/(2\times Fc)\}] \quad (1)$$

and, $$f\text{value}=1/(2\times NA) \quad (2)$$

where D is the diameter (if circular) of aperture stop 110 and Fc is the effective off-axis focal length of collimating mirror 105. The NA and fvalue can be generalized by an "averaged NA" or averaged fvalue if D is non-circular.

A greater fvalue (smaller NA) will cause less total light to reach image plane 195. Prior art echelle spectrographs comprise approximately f/7 or greater systems. In contrast, Applicant's echelle spectrograph 100 effectively comprises an f/3 or faster optical system (NA>0.15). This represents approximately a 10× improvement in light throughput compared to prior art devices.

The total amount of light through entrance aperture 101 is defined by the etendue (E) of the system at aperture stop 110. At aperture stop 110, E is proportional to the product of entrance aperture 101 area and the solid angle of the light passing through entrance aperture 101. Therefore, increasing either the solid angle (proportional to either 1/{fvalue2} or NA2) of light passing through entrance aperture 101 or increasing the area of entrance aperture 101 will increase total throughput (E) of the instrument. However, as those skilled in the art will appreciate, in general, the spectral resolution (defined by the full width at half maximum of a spectral emission line, FWHM) of an instrument is approximately proportional to the width of entrance aperture 101.

As those skilled in the art will further appreciate, the light passing through echelle spectrograph 100 contains multiple spectral orders that are separated, or dispersed, as light passes through prism 140. Furthermore, the height of entrance aperture 101 must be less than the distance between the spectral orders at image plane 195, or cross-talk between the spectral orders will occur. Therefore, the size of the entrance aperture 101 is limited in both height and width to provide good spectral order separation and high spectral resolution at image plane 195. The best way to increase throughput is to decrease the effective fvalue (increase NA).

It is important to note that the light source must be optically coupled to entrance aperture 101. Furthermore, to maximize throughput of light, the fvalue of the optics associated with the light source must perfectly match the fvalue of the input optics defined by Fc and D in module 102 (see equations 1 and 2). Each embodiment of the light source can have a very different fvalue. For example, the typical effective fvalue of an optical fiber is f/2.3 (NA=0.22) and the fvalue of a telescope can be f/16 or higher.

In certain embodiments, Applicant's echelle spectrograph 100 can have collimating mirror 105 of a different focal length without changing the mirror diameter. For example, if the focal length of collimating mirror 105 is doubled, then the fvalue of the collecting optics as defined by Equation 2 is increased by a factor of about 2 (NA is half) if D remains unchanged. The magnification of echelle spectrograph 100 is defined by the effective ratio of module 104 (Fi) to module 102 (Fc):

$$M=Fi/Fc \quad (3)$$

When Fc is doubled, M is halved. The image of entrance aperture 101 projected onto image plane 195 at a given wavelength (or equivalently, the FWHM of a spectral emission line) will then be approximately half the size as with the original module 102. It is therefore possible to double entrance aperture 101 (in both height and width) to preserve the total throughput or etendue of echelle spectrograph 100 without degrading spectral resolution or changing any of the optics.

Applicant's echelle spectrograph 100 can match any light source from approximately f/2 to >f/16 while maximizing etendue by simply changing Fc and the diameter of the entrance aperture 101. At the same time, the spectral resolution and order overlap will remain unchanged. The image quality and order location at image plane 195 will also remain unchanged as long as entrance aperture 101 is at the correct location (with the appropriate size) and D remains unaltered.

The correcting field lens 190 not only adds two more corrective optical surfaces, but also allows for longer effective focal length of the echelle spectrograph 100. Further, the field lens 190 together with the position of the first mirror 150 make the echelle spectrograph 100 more compact. When optimizing the first surface 192 and the second surface 194 of the field lens 190, the concave surface of the second mirror 160, the convex surface of the third mirror 170, and the concave surface of the fourth mirror 180 simultaneously, optical aberrations of the echelle spectrograph 100 are reduced compared to optimizing only the concave surface of the second mirror 160, the convex surface of the third mirror 170, and the concave surface of the fourth mirror 180 simultaneously. Moreover, the useable size of a sensor is increased, i.e., a much larger corrected area at the image plane 195, therefore a longer focal length can be with the same spectral orders on a sensor.

As those skilled in the art will appreciate, the longer focal length of the echelle spectrograph 100 will result in higher spectral resolving power (wavelength/FWHM). In certain embodiments, the spectral resolving power of the echelle spectrograph 100 is up to 200,000.

Moreover, as those skilled in the art will appreciate, because the spectral orders are located further apart due to the larger useable size of the sensor so a taller entrance aperture 101 can be used without interference between adjacent spectral orders. For example, without employing the field lens 190, the maximum size of the entrance aperture 101 is about 25 mm without causing too much aberrations. When a field lens 190 is employed, the maximum size of the entrance aperture 101 is about 56 mm without causing too much aberrations. Employing the field lens 190 allows a combination of better spectrograph throughput (taller slit) and better resolving power (higher dispersion).

Each of U.S. Pat. No. 7,936,454 and U.S. Pat. No. 7,936,455 is incorporated by reference in its entirety to describe the laser induce breakdown spectroscopy (LIBS) implementations of the echelle spectrograph 100.

While the preferred embodiments of the present invention have been illustrated in detail, it should be apparent that modifications and adaptations to those embodiments may occur to one skilled in the art without departing from the scope of the present invention.

I claim:

1. A spectrograph which includes five mirrors in radiative communication, comprising:
    a first mirror having a flat mirror reflective surface and positioned to reflect light traversing a prism;
    a second mirror having a concave-shaped reflective mirror surface and positioned to reflect light received from the first mirror;
    a third mirror having a convex-shaped reflective mirror surface and positioned to receive light reflected by the second mirror;
    a fourth mirror having a spheroidal reflective mirror surface and in positioned to receive light reflected by the second mirror; and
    a field lens comprising a concave mirror surface in combination with a convex mirror surface, wherein light received by said field lens from said fourth mirror enters said convex mirror surface, traverses said field lens, and exits from said concave mirror surface.

2. The spectrograph of claim 1, further comprising:
    an entrance aperture to receive light from a source; and
    a collimating mirror to reflect the light in a collimated pattern towards a first aperture stop, the first aperture stop being disposed along an optical axis of the collimating mirror.

3. The spectrograph of claim 2, further comprising:
    a diffraction grating to receive light from the collimating mirror; and
    a prism in optical communication with the diffraction grating to receive and diffract light that has passed through the entrance aperture into a plurality of beams dispersed by wavelength and directed onto the dispersive prism.

4. The spectrograph of claim 3, wherein said spheriodal fourth mirror comprises a concave reflective surface.

5. The spectrograph of claim 3, wherein:
    the prism is disposed between the diffraction grating and the first mirror; and
    the prism forms light comprising a plurality of spectral orders.

6. The spectrograph of claim 1, further comprising:
    a fiber optic cable input; and
    a sensor comprising an image plane to receive light reflected from the fourth mirror on the image plane.

7. The spectrograph of claim 6, wherein:
    the field lens is disposed between the fourth mirror and the sensor such that a plurality of beams reflected from the fourth mirror passes into and through a first spherical and convex surface, passes through said field lens, and exits the field lens through a second spherical and concave surface, and is received by the image plane.

8. The spectrograph of claim 7, wherein the field lens is positioned such that the second mirror, third mirror, fourth mirror, and field lens share a common vertex axis.

9. The spectrograph of claim 7, further comprising a second aperture stop disposed between the fourth mirror and the field lens such that a plurality of the beams reflected from the fourth mirror passes through the second aperture stop and onto the first spherical and convex surface of the field lens.

10. The spectrograph of claim 9, wherein the second aperture stop does not eliminate the common vertex axis.

11. The spectrograph of claim 1, further comprising a baffle formed to include an aperture, wherein the baffle is positioned such that the light reflected from the second mirror passes through the aperture at an intermediate focus and is directed onto the third mirror.

12. A method of laser induced breakdown spectroscopy (LIBS) using the spectrograph of claim 8, the method comprising:
    setting a sensor to a first mode, wherein the first mode is a non-integrating idle mode;
    energizing a lasing device;
    emitting a laser pulse to produce a plasma at a radiation source; and
    setting the sensor to a second mode a few microseconds after the laser pulse is emitted.

13. The method of claim 12, wherein the collimating mirror is adapted to receive and reflect radiation received through an entrance aperture in a collimated pattern towards a first aperture stop, wherein the first aperture stop is located along a parent optical axis of the collimating mirror, said method further comprising capturing at said entrance aperture an emission spectrum formed by atoms and ions disposed within said plasma.

14. The method of claim 12, further comprising acquiring an image using the sensor.

15. The method of claim 12, further comprising:
    reading the image from the sensor;
    downloading the image to a computing device; and
    linking and linearizing a plurality of spectral orders to form a spectral curve.

16. The spectrograph of claim 8, further comprising:
    a processor and a non-transitory computer readable medium having computer readable program code encoded therein to analyze an emission spectrum formed using laser induced breakdown spectroscopy (LIBS), the computer readable program code comprising a series of computer readable program steps to effect:
    setting the sensor to a first mode, wherein the first mode is a non-integrating idle mode;
    energizing a lasing device to produce a plasma at a radiation source;
    emitting a laser pulse; and
    setting the sensor to a second mode a few microseconds after the laser pulse is emitted.

* * * * *